(12) United States Patent
Nabarro et al.

(10) Patent No.: US 6,640,460 B1
(45) Date of Patent: Nov. 4, 2003

(54) MEASURING DEVICE AND METHOD

(75) Inventors: Daniel Joseph Nunes Nabarro, London (GB); Alun Wilcox, Surrey (GB); Timothy Roland Manson, London (GB); Julian Francis Ralph Swan, London (GB)

(73) Assignee: T-Bra Limited, London (GB)

( * ) Notice: Subject to any disclaimer, the term of this patent is extended or adjusted under 35 U.S.C. 154(b) by 0 days.

(21) Appl. No.: 10/110,814

(22) PCT Filed: Oct. 18, 2000

(86) PCT No.: PCT/GB00/04005

§ 371 (c)(1),
(2), (4) Date: Jul. 5, 2002

(87) PCT Pub. No.: WO01/29501

PCT Pub. Date: Apr. 26, 2001

(30) Foreign Application Priority Data

Oct. 18, 1999 (GB) .............................................. 9924618
Jul. 4, 2000 (GB) .............................................. 0016464

(51) Int. Cl.⁷ .............................. G01B 3/10; A61B 5/107
(52) U.S. Cl. .............................. 33/759; 33/770; 33/512
(58) Field of Search ........................... 24/31 R, 32, 194; 33/511, 512, 514.1, 555.1, 555.4, 755, 758, 759, 768, 770

(56) References Cited

U.S. PATENT DOCUMENTS

| 650,389 | A | * | 5/1900 | Hatfield ...................... 33/555.4 |
| 2,262,664 | A | * | 11/1941 | Bresson ...................... 33/555.4 |
| 2,428,980 | A | | 10/1947 | McCann |
| 2,559,501 | A | * | 7/1951 | Graf .............................. 33/512 |
| 3,292,261 | A | * | 12/1966 | Hayes .......................... 33/759 |
| 3,639,995 | A | * | 2/1972 | Gardner ...................... 33/514.1 |
| 3,685,155 | A | * | 8/1972 | Oblander ...................... 33/755 |
| 3,918,166 | A | | 11/1975 | Mason |
| 4,211,011 | A | * | 7/1980 | Jacobson ...................... 33/759 |
| 4,433,486 | A | | 2/1984 | Muehlenbein |
| 4,473,949 | A | * | 10/1984 | Schechtman .................. 33/512 |
| 4,878,271 | A | * | 11/1989 | Kitokovsky ................... 24/194 |
| 4,920,659 | A | | 5/1990 | Becher |
| 5,269,069 | A | * | 12/1993 | Min ........................... 33/514.1 |
| 5,406,715 | A | * | 4/1995 | Koizumi et al. ............... 33/770 |
| 5,619,804 | A | * | 4/1997 | Vogt et al. ..................... 33/759 |
| 5,732,475 | A | | 3/1998 | Sacks et al. |
| 6,178,652 | B1 | * | 1/2001 | Foster .......................... 33/511 |
| 6,253,459 | B1 | * | 7/2001 | Barnhill ...................... 33/514.1 |
| 6,276,069 | B1 | * | 8/2001 | Chadwick et al. ............ 33/512 |

FOREIGN PATENT DOCUMENTS

| EP | 0 821 909 A2 | 2/1998 |
| GB | 834469 | 5/1960 |
| GB | 2 106 250 A | 4/1983 |

* cited by examiner

Primary Examiner—G. Bradley Bennett
(74) Attorney, Agent, or Firm—Stevens & Showalter LLP

(57) ABSTRACT

The present invention encompasses a measuring tape for measuring the torso girth of a user, the tape comprising a separable fastening that, when fastened, creates a loop of tape that extends in use around the user's torso without support from the user's hands, a link co-operable with the tape allowing the circumference of the loop to be adjusted or varied when around the user's torso, and girth indicia co-operable with the link to indicate the circumference of the loop. The link maintains a securing tension on the loop to secure the loop around the torso but allows expansion of the loop when the user expands her torso during said measurement, and resists variation of the loop circumference when the fastening is unfastened after use. In this way, the circumference of the loop can be read by the user after use with reference to the girth indicia A method for measuring the torso girth of a user by means of the present invention is also contemplated.

24 Claims, 11 Drawing Sheets

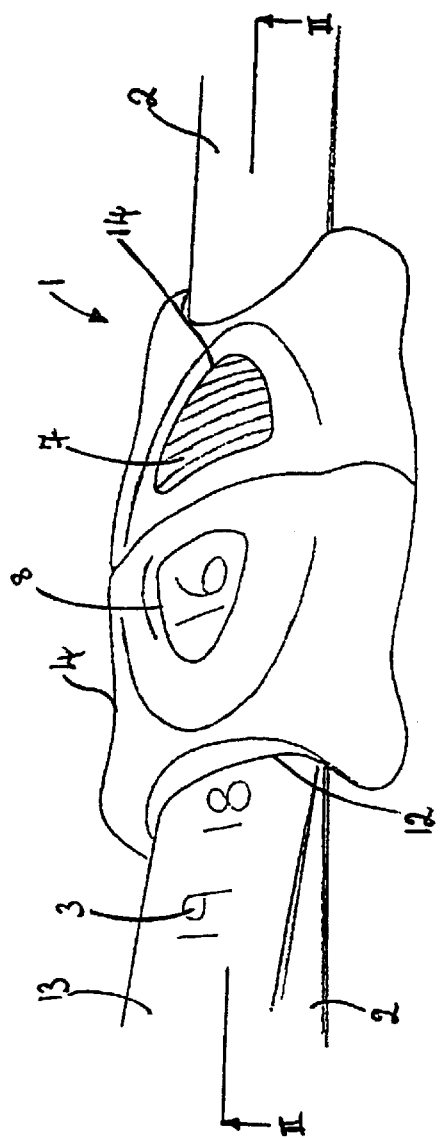
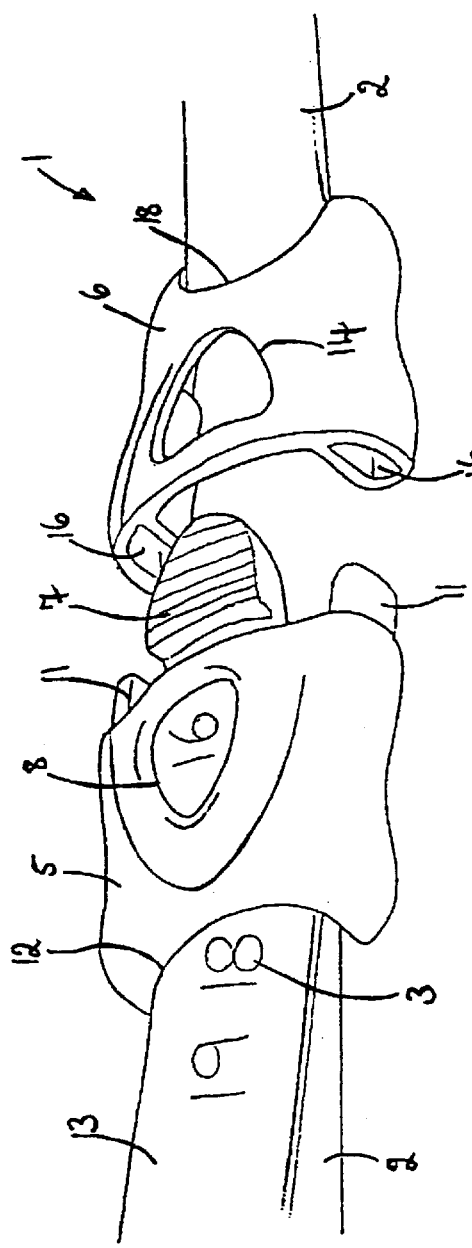
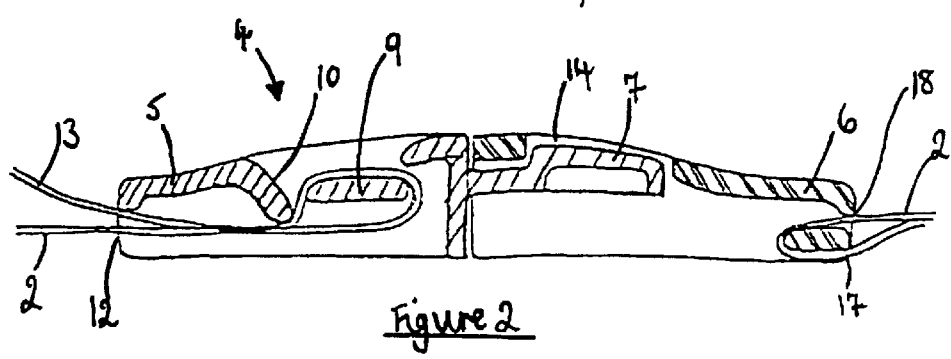

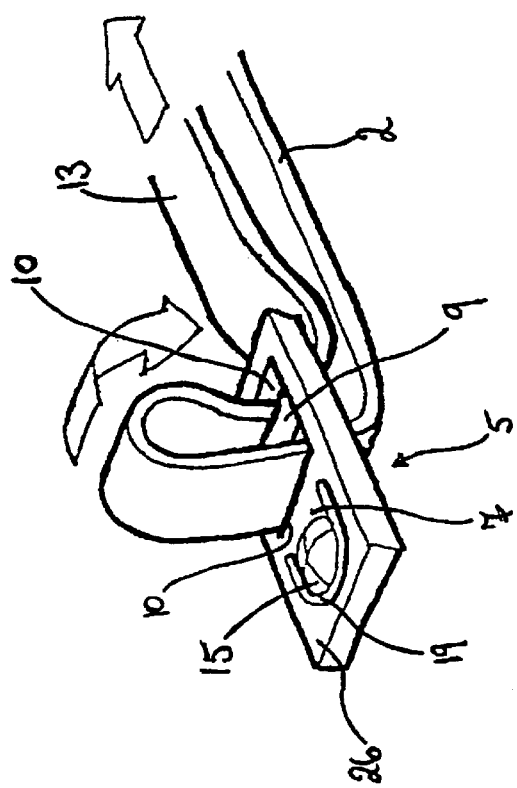
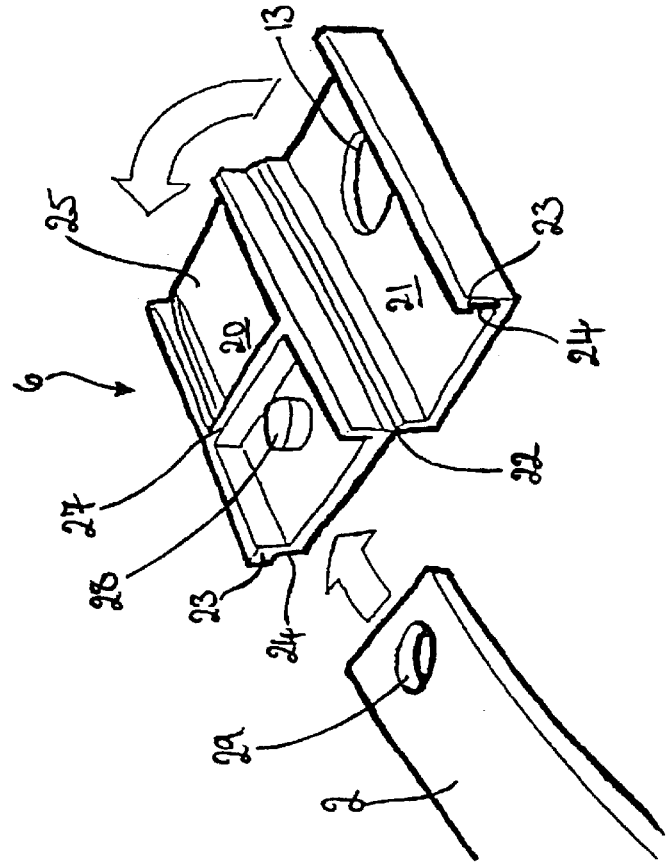
Figure 3

MEASURING DEVICE AND METHOD

BACKGROUND OF THE INVENTION

The present invention relates to a device and method of self-measurement for the fitting of bras and other close-fitting clothing. In exemplary embodiments, the invention relates to the accurate measurement of a torso underneath or around the breasts for the correct fitting of a bra.

In this specification, the term 'bra' will be used conveniently to encompass all clothing designed closely to fit a wearer's breasts, thus including other forms of lingerie such as body suits, as well as swimwear and other sportswear such as leotards. However, although bras will be referred to herein to exemplify the invention, the invention is not limited to measurement of breast size for the purpose of fitting bras but instead enjoys wider application to other body measurement, especially around the torso at chest, waist or hip level, around the neck, or around the limbs.

It is important for a bra to fit correctly, not only for comfort, but because an ill-fitting bra can cause a variety of health problems, including muscle ache, irritable bowel syndrome and even spinal injuries.

Unfortunately, bra fitting is bedevilled by problems, including variations in size, shape and disposition of the breasts, by the amorphous nature of the breasts themselves, and by the fact that many women are never measured for bra size, either professionally or otherwise. Nevertheless, when buying a bra, most women know from previous experience roughly the size that is required This is always an approximation as changes in chest size, as well as changes to the size and shape of breasts, occur at different times during the menstrual cycle and as the years progress. Also, substantial and often irreversible changes in breast size and shape can occur during and after pregnancy.

A typical way to chose a bra is either by choosing a favourite style or make, regardless of the accuracy of the fit, or to try on a selection of styles in a range of sizes and makes. In this way, best fit is ascertained by trial and error. Both processes take time, are dependent on available stock and do not always result in the purchase of a properly fitting bra.

For women who are unsure of their size, some retail outlets provide a bra measuring service whereby measurements are taken either with or without a bra being worn. Apart from the advantage of obtaining expert advice or at least a second opinion as to fit, professional measuring services have many drawbacks. For example, if the measurement is taken with a bra on, there is the advantage that the breasts are supported but the resulting measurement may be inaccurate if the bra is not an accurate fit to start with. If the measurement is taken without a bra being worn, the measurement will also be inaccurate since the breasts are unsupported and therefore are of a different shape and volume compared to when they are supported.

The significance of support is that a breast is largely constituted of fatty tissue having a resiliently compressible, gelatinous consistency whose shape and volume will adapt to some extent to suit a receptacle such as a bra cup in which the breast is contained. When there is no such support, gravity will change both the shape and volume of the breast, obviously with increasing effect the greater the size and weight of the breast.

Even a professional measuring service is not immune from the drawback that the accuracy of breast and torso measurement for fitting a bra will usually depend on the level of training and experience of the person doing the measuring. It is also true that bra-fitting experts apply an element of subjectivity to their work. The aim of such experts is not to arrive at a universal bra size measurement that the user can apply with confidence to bras in general, but instead to fit the consumer to one of the bras available in stock, the purpose of measurement therefore being to select a limited range of bras that the user can try on and select from. Such trial and error is all well and good in a store environment if the consumer has the time and inclination to visit the store, but it does not suit the mail order and Internet shopping methods that many consumers increasingly prefer.

A further problem with professional measuring services is that many women feel uncomfortable about being measured in a semi-naked state by a stranger. As a result, the measurement/fitting may be hurried and incorrect advice given.

Self-measuring guides are therefore available. These generally involve measuring the circumference of the torso under the breasts to obtain a torso measurement, followed by taking a measurement across the breasts at the largest point, i.e. across the nipples in an 'over-bust' measurement. Then, these measurements are put into a formula to work out a nominal torso and bra cup size. The bra cup size is related to torso size and also to the difference between torso size and over-bust measurement. In other words, the difference between torso size and over-bust measurement imputes a cup size for a given torso size. However, the product of the formula is only as good as the measurements that are put into the formula, and unfortunately those measurements are often inaccurate.

For example, as noted above, a certain level of expertise is required to achieve any degree of accuracy; one could hardly expect an inexpert woman, usually working on her own, to match the accuracy of measurement of an experienced bra-fitter. In particular, it is difficult to be sure that a measuring tape is held at an appropriate tension and in the correct position, which is especially difficult to ascertain across the back, either with or without the aid of a mirror. Also, the cross-nipple or over-bust measurement introduces an inherent inaccuracy because it does not take proper account of the effect of the varying depth and width of the cleavage between the breasts. The measuring tape bridges the cleavage rather than following the contour, and so cannot accurately tell if a particular apparent breast size is due to the degree of separation and protrusion of the breasts rather than the overall breast size.

Furthermore, the final measurement will be dependent on the type of bra being worn, it being noted that measurement often takes place while wearing a bra and that different bras impose different shapes upon the breasts that they support. A particular source of inaccuracy arises where the bra is designed to flatten the breast or maximise cleavage because such distortion of the breasts gives a misleading over-bust measurement. In general, there is a tendency to overestimate torso size and to underestimate over-bust measurement: as cup size is imputed from t he difference between those measurements and with regard to the torso size, the combination or sum of errors in these critical measurements magnifies errors in apparent cup size.

Consequently, many women wear ill-fitting bras that are uncomfortable and provide insufficient support, which has adverse effects on posture and shape in later years. The correct fitting of a bra is especially important while breasts are developing during the teenage years and incorrect fitting during this time can lead to complications in later years.

Torso girth measurement is typically obtained by passing a tape measure around the torso underneath the breasts, holding the tape measure between a finger and thumb, tensioning the tape until it feels comfortably tight, and noting the resulting measurement. A fixed margin is added to the measurement to give the chest size required, adding further vagaries to the measurement. In the United Kingdom, such a measurement is usually obtained in inches, while in Europe, centimetres are the common unit. In the UK imperial scale, bra chest sizes increment in even-numbered two-inch steps e.g. 32 inches, 34 inches, 36 inches and so on. Accordingly, a margin of four inches (10 cm) is added if the measured chest size is an even number and a margin of five inches (12.5 cm) is added if the measured chest size is an odd number.

It will be appreciated that it is not easy to ensure that the tape measure is correctly aligned and indeed correctly tensioned. Nor is it easy to handle a flexible tape measure whose overlapping ends must be held accurately during measurement. In particular, difficulties of reading from the scale of the tape measure are compounded by the use of a mirror or, if direct viewing is attempted, by the presence of the user's breasts, which tend to get in the way. In view of that, many women attempt to measure their torso size by pinching an overlapping portion of the tape measure between thumb and forefinger and keeping hold of the appropriate portion of the tape when the tape is removed from around the torso. There is a risk that the tape will slip in the user's grasp during that movement and so give a false reading. There is also the certainty that the width of the user's thumb and fingers precludes a fully accurate measurement.

Alignment of a measuring tape is difficult to ascertain, and more difficult to ensure. Checking alignment of the tape across one's back requires peering into a mirror and this involves movement of the torso that may in itself disturb correct alignment.

Tension in the tape around the torso is especially important yet more difficult to gauge correctly: specifically, consistency of girth measurement is difficult to achieve when encircling a compressible body such as a torso, especially when there is a significant depth of body fat. The problem is that pulling on a strap or tape to ensure that it is taut compresses the body encircled by the strap or tape, and so the girth of the body will change as a result of the measurement process. This introduces self-defeating inaccuracy.

It has been shown that bras that fit too loosely around the torso do not properly support the breasts, while bras that fit too tightly around the torso compress the rib cage and diaphragm causing a number of complications, including poor digestion and constipation. Unless a woman is being measured professionally, she is unlikely to know the required tension, and even professional measurers may have difficulty in achieving the correct tension. Indeed, it is customary for professional measurers to tension a tape so it is tight around the woman's chest and then to ask her to breathe in or raise her shoulders to expand her chest. This causes the tape to relax to an extent necessary to ensure comfort in all modes of use. For the aforementioned reasons, this method of measurement is difficult for a woman to perform on her own. It is also difficult to perform objectively.

It is against this background that the present invention has been made. Accordingly, the invention aims to provide an accurate measurement of a torso which facilitates the selection of the correct bra size to suit an individual's requirements. In this way, a measurement made by a woman in her own home will be as accurate as one made by a professional measurer in a retail outlet.

SUMMARY OF THE INVENTION

From one aspect, the invention encompasses a measuring tape for measuring the girth of any part of a user's body and especially any part of the user's torso such as the waist, chest (including around the user's breasts) or hips. In the example of torso measurement, the tape comprises a separable fastening that, when fastened, creates a loop of tape that extends in use around the user's torso without support from the user's hands, a link co-operable with the tape allowing the circumference of the loop to be adjusted or varied when around the user's torso, and girth indicia co-operable with the link to indicate the circumference of the loop, wherein the link maintains a securing tension on the loop to secure the loop around the torso but allows expansion of the loop when the user expands her torso during said measurement, and resists variation of the loop circumference when the fastening is unfastened after use so that the circumference of the loop can be read by the user after use with reference to the girth indicia. Thus, torso girth measurement is simple, quick, easy and accurate.

For simplicity and ease of manufacturing, it is preferred that the link is integral with the fastening.

Whilst it is further preferred that the girth indicia are situated on the tape, the link may be separate from the fastening and connected to the fastening by a strip movable with respect to the link. In which case, the girth indicia, such as numerals, icons or colours, may be situated on the strip.

Advantageously, the link includes a display area, such as a window or cut-out, with which indicia can align to be displayed. It will be apparent that the size and shape of the display area will be tailored to allow the whole indicia to be displayed. For example, a window may be rectangular or oval in shape.

It is further preferred that the link is a slipping link that allows slippage of the tape to allow expansion of the loop while maintaining the securing tension, but grips the tape to an extent necessary to prevent slippage of the tape when the fastening is unfastened after use. This allows the user to adjust the tape without having to hold it herself under the correct tension.

Conveniently, the slipping link includes a holding bar around which the tape is looped and one or more gripping formations bearing upon the tape looped around the bar. In this way, the tape follows a tortuous path and is restricted from slipping by friction between the holding bar, the one or more gripping formations and the tape.

Optionally, the link may be a store of tape that retracts tape on contraction of the loop and pays out tape on expansion of the loop. It is advantageous if the store of tape is a reel biased to retract the tape. Such an embodiment allows the tape to be stored compactly predisposing it, for example, for multiple use by a professional measurer in a retail outlet, or to be sent by mail for an individual to use in the comfort of her own home.

In a further embodiment, or in addition, the link may be adapted for indexible movement of the tape between discrete detent positions. The detent positions ideally correspond to the spacing between successive indicia Indexing movement may be achieved by a notch and tooth arrangement, a sprung arm or pawl mechanism, for example.

In order to gauge accurately when the correct tension in the loop has been reached, a further advantage is seen if the tape includes a tension indicator for indicating tension in the loop.

In a preferred embodiment, the tension indicator comprises first and second parts linked by resilient bias means for relative movement against bias when the loop is under circumferential tension. Advantageously, a visual indicator responsive to the extent of said relative movement is included. It will be appreciated that the resilient bias means may be in the form of a tension spring or any other suitable means.

Preferably, the visual indicator comprises tension indicia associated with one of said parts of the tension indicator being relatively movable into alignment with a window, cut-out or indicating indicia on the other of said parts of the tension indicator. For clear instructions to the user, the tension indicator indicia may be in the form of confirmatory indicia, such as a tick and/or green colour.

Advantageously, the tension indicia is situated on a portion of tape attached to one of said parts of the tension indicator.

From another aspect, the invention resides in a method for measuring the girth of any part of a user's body, especially any part of the user's torso such as the waist, chest (including around the user's breasts) or hips. In the example of torso measurement, the method comprises fastening a loop of tape around the user's torso without support from the user's hands, creating and maintaining a securing tension on the loop to secure the loop around the torso, permitting expansion of the loop when the user expands her torso during said measurement, unfastening the loop while maintaining the loop circumference, and reading the circumference of the loop after use.

Preferably, the method further comprises viewing a visual indication of the tension in the loop and advantageously further comprises the step of responding to the visual indication by adjusting the tension in the loop to achieve an indicated predetermined tension.

References in this specification to any part of the user's body are to be construed broadly as encompassing the neck and limbs as well as parts of the user's torso.

BRIEF DESCRIPTION OF THE DRAWINGS

In order that the invention may be more easily understood, reference will now be made, by way of example, to the accompanying drawings, in which:

FIGS. 1A and 1B are perspective views of a first embodiment of the invention, showing the clasp portions connected (FIG. 1A) and disconnected (FIG. 1B);

FIG. 2 is a longitudinal cross-section view along line II—II of FIG. 1A;

FIG. 3 is an exploded perspective view of a second embodiment that works in a manner akin to the first embodiment;

DETAILED DESCRIPTION OF THE INVENTION

Figure 4:
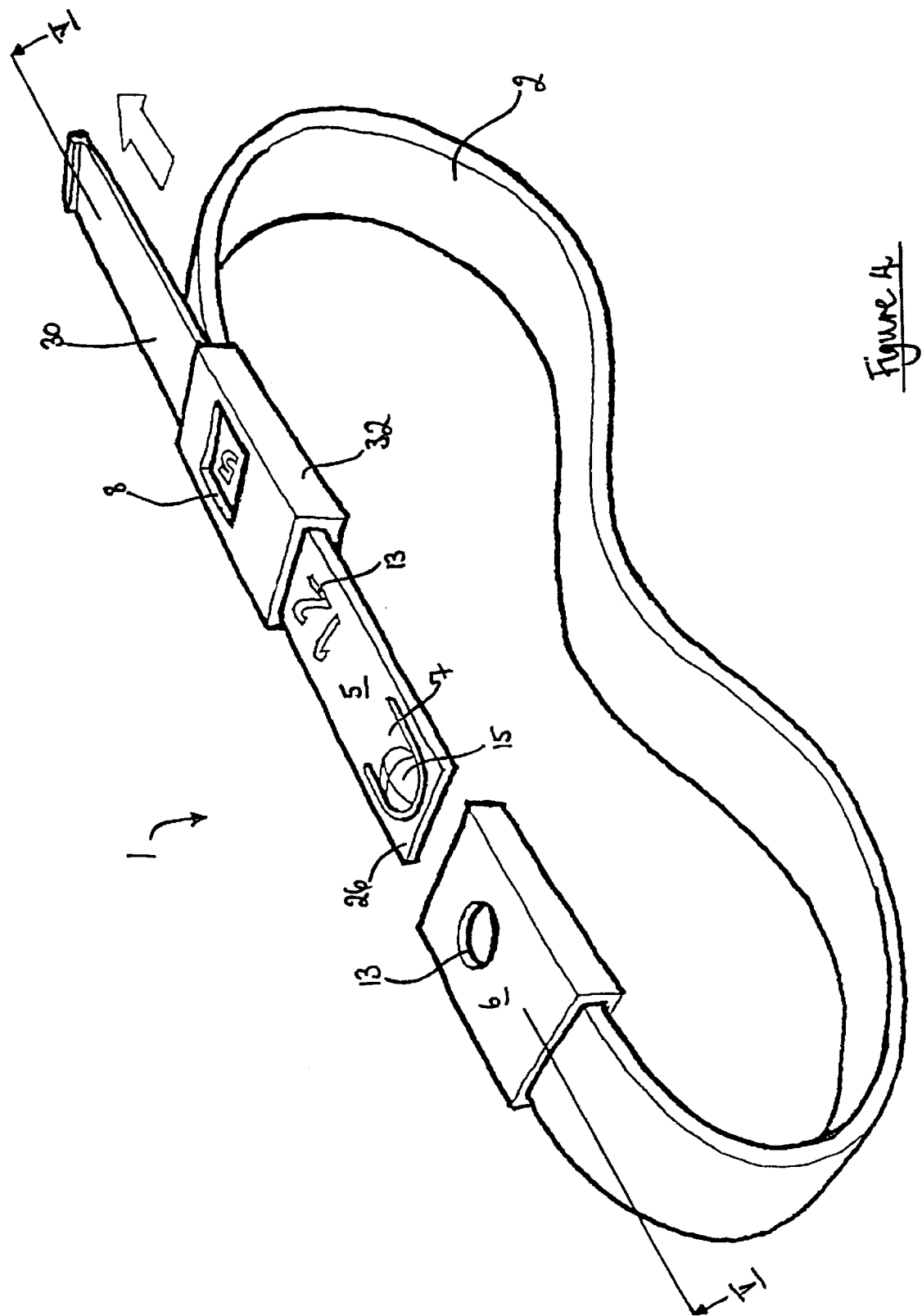
FIG. 4 is a perspective view of a third embodiment of the invention.

Referring firstly to FIG. 1A, FIG. 1B and FIG. 2, a torso measuring device 1 has a torso strap 2 just over 1 meter in length. The strap 2 bears indicia 3 marked, for example by printing or stamping, at regular intervals along part or all of the length of the strap 2. The indicia 3 represent a scale that runs from one end of the strap 2 towards the other.

A clasp 4 comprises two interconnecting portions, namely a male portion 5 and a female portion 6, both of which are attached to respective portions of the strap 2. The male portion 5 is slidably attached to an intermediate portion of the strap 2 whereas the female portion 6 is fixed to an opposed end of the strap 2.

The male portion 5 of the clasp 4 is moulded to incorporate a resilient tongue 7, a window 8, a holding bar 9 disposed below the window 8, a gripping formation 10 opposed to the holding bar 9, and two lugs 11, one disposed each side of the tongue 7. As best shown in the cross-sectional view of FIG. 2, the strap 2 loops back on itself within the male portion 5. Specifically, the strap 2 enters the male portion 5 via a distal aperture 12, loops around the holding bar 9, between the holding bar 9 and the gripping formation 10, and back out through the distal aperture 12. Between them, the holding bar 9 and the gripping formation 10 provide sufficient friction to hold together the male portion 5 and the strap 2 when the strap 2 is under overall tension but allow the strap 2 to slip within the male portion 5 when a free end 13 of the strap 2 is pulled.

It will be noted that when the strap 2 is threaded within the male portion 5 as described, the holding bar 9 acts as a platen that supports a portion of the strap 2 for viewing through the window 8. In use, the appropriate indicia 3 can be read off by looking in the window 8.

The female portion 6 is moulded to complement the male portion 5 and has a hole 14 that receives an enlarged free end of the interconnecting tongue 7 in a snap-fit arrangement when the male and female portions 5, 6 are brought together and the former is inserted into the latter. The lugs 11 of the male portion 5 locate within corresponding recesses 16 moulded in the female portion 6. To disconnect the two portions, the enlarged free end of the tongue 7 protruding within the hole 14 is depressed and pushed clear of the female portion 6.

A fixing bar 17 within a distal aperture 18 of the female portion 6 fixes an end of the strap 2 to the female portion 6. As shown in FIG. 2, that end of the strap 2 loops around the fixing bar 17 and can simply be sewn or bonded back on itself to secure the loop.

In use of the measuring device 1, the strap 2 is passed around the user's torso and underneath the breasts in such a way that the clasp 4 can be fastened at the front of the user's torso. Once fastened in this way, the free end 13 of the strap 2 protruding from the male portion 5 is pulled away from the clasp 4 until the strap 2 is tensioned tightly around the torso. The tension on the strap 2 is then increased by the user expanding her rib cage, for example by taking in a large breath. This causes the strap 2 to slide over the holding bar 9 so that the loop of strap 2 around the user's torso is allowed to lengthen to an extent necessary to ensure a comfortable fit of a bra in all modes of use. That done, the clasp 4 is unfastened, the strap 2 is removed from around the torso and the indicia 3 on the strap 2 shown in the window 8 of the male portion 5 is noted.

In this way, the measuring device 1 makes torso girth measurement simple, quick, easy and accurate. The user merely has to fasten together the two portions of the clasp 4 and then has both hands free to adjust the alignment of the strap 2 around the torso, to tension it appropriately and to make sure that the alignment of the strap 2 remains correct while the torso is expanded. The measuring device 1 is configured to maintain an appropriate degree of tension throughout the measuring process, even through the slippage necessary to allow torso expansion.

Referring now to FIG. 3 of the drawings, the second embodiment shown therein has features akin to those of the first embodiment and so like numerals will be used for like parts. The clasp 4 shown in FIG. 3 has a generally flat, oblong male portion 5 moulded to define a holding bar 9 around which the strap 2 is looped and tensioned with the aid of gripping formations 10 on each side of the holding bar 9, as indicated by the adjacent arrows. Unlike the first embodiment, the indicia 3 (not shown) on the strap 2 are not read through a window but merely where the strap 2 is exposed as it passes over the holding bar 9.

The tongue 7 is integral to the male portion 5 and includes a raised convex button 15 corresponding to the enlarged portion of the tongue 7 of the first embodiment. The tongue 7 is resiliently movable in relation to the reminder of the male portion 5 by virtue of a U-shaped slot 19 penetrating the male portion 5. The button 15 locates within a hole 13 of the female portion 6 as will be explained.

The female portion 6 has a base 20 to which a lid 21 is integrally attached by a flexible web 22 acting as a hinge, the female portion 6 being completed by closing the lid 21 over the base 20 as indicated by the arrow. The lid 21 is held closed by a snap-fit between co-operating elongate lip and recess formations 23, 24 on the lid 21 and the corresponding part of the base 20. The lid 21 includes a hole 13 through which the button 15 on the tongue 7 protrudes when the male and female portions 5, 6 are connected together, to which end the base 20 includes a channel 25 for receiving the proximal end 26 of the male portion 5, including the tongue 7.

The channel 25 terminates in a transverse partition 27 upstanding from the base 20, on the other side of which is a fixing pillar 28 also upstanding from the base 20. The end of strap 2 to be connected to the female portion 6 has a fixing hole 29 that receives the fixing pillar 28, as indicated by the adjacent arrow. The strap 2 is secured within the female portion 6 when the lid 21 is snap-fitted closed onto the base 20, with the fixing pillar 28 held within the fixing hole 29.

Figure 5:
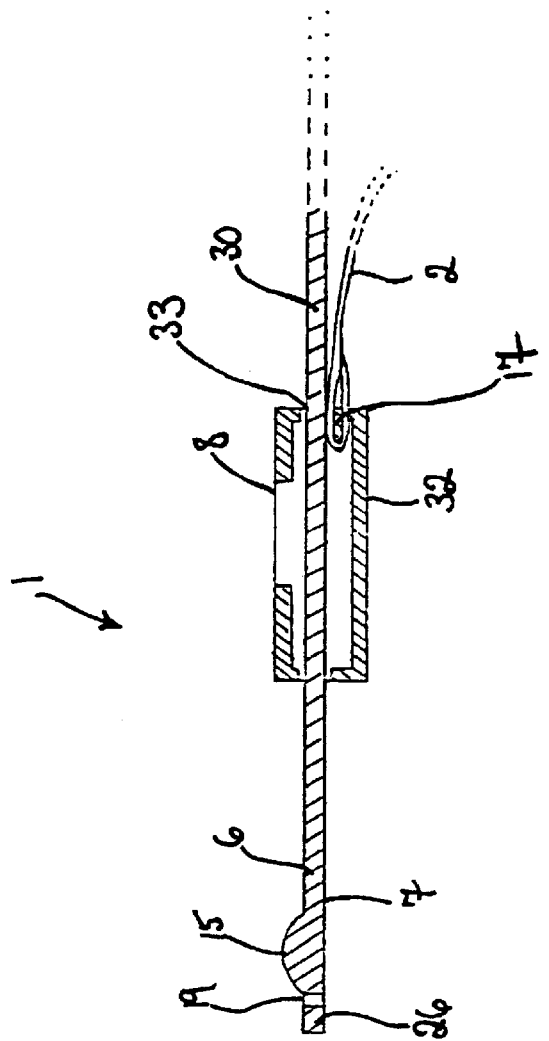
FIG. 5 is a longitudinal cross-section view along line V—V of FIG. 4.

A third embodiment of the invention is illustrated in FIGS. 4 and 5. FIG. 4 shows a measuring device 1 with a clasp which is similar to the clasp 4 shown in FIG. 3. Again, therefore, like numerals are used for like parts. It will be noted in particular that the female portion 6 is identical to the female portion 6 of FIG. 3 (save that the lid 21 is closed onto the base 20) and that the proximal end 26 of the male portion 5, with its integral tongue 7 and button 15, is the same as the corresponding part in FIG. 3. As best shown in the cross-sectional view of FIG. 5, the first end of the strap 2 is anchored within the female portion 6 in the same manner as the embodiment of FIG. 3.

In the third embodiment, the male portion 5 of the clasp 4 is defined by a first end of a semi-rigid strip 30 that passes slidably through a sleeve 32 to which the second end of the strap 2 is fixed. As shown in cross-section in FIG. 5, the second end of the strap 2 is looped around a fixing bar 17 in a distal aperture 33 in the sleeve 32, akin to the fixing bar 17 shown in FIG. 2. The strip 30 also extends through this distal aperture 33.

The sleeve 32 includes a window 8 and indicia 3 are marked at regular intervals along the strip 30 instead of the strap 2, so that appropriate indicia 3 will be displayed in accordance with the position of the strip 30 with respect to the sleeve 32. This accords to the size of the loop defined by the strap 2 and the portion of the strip 30 protruding proximally from the sleeve 32.

The measuring device 1 of the third embodiment is used in much the same way as described above, in that the strap 2 is passed around the torso and underneath the breasts so the clasp 4 is fastened at the front of the user's torso. The strip 30 is pulled in the direction shown by the arrow until the strap 2 is tensioned tightly around the torso. As before, the tension is increased by expanding the rib cage, causing the strip 30 to slide proximally within the sleeve 32. The final torso girth measurement is read through the window 8 in the sleeve 32 once the clasp 4 has been undone.

Figure 6A:
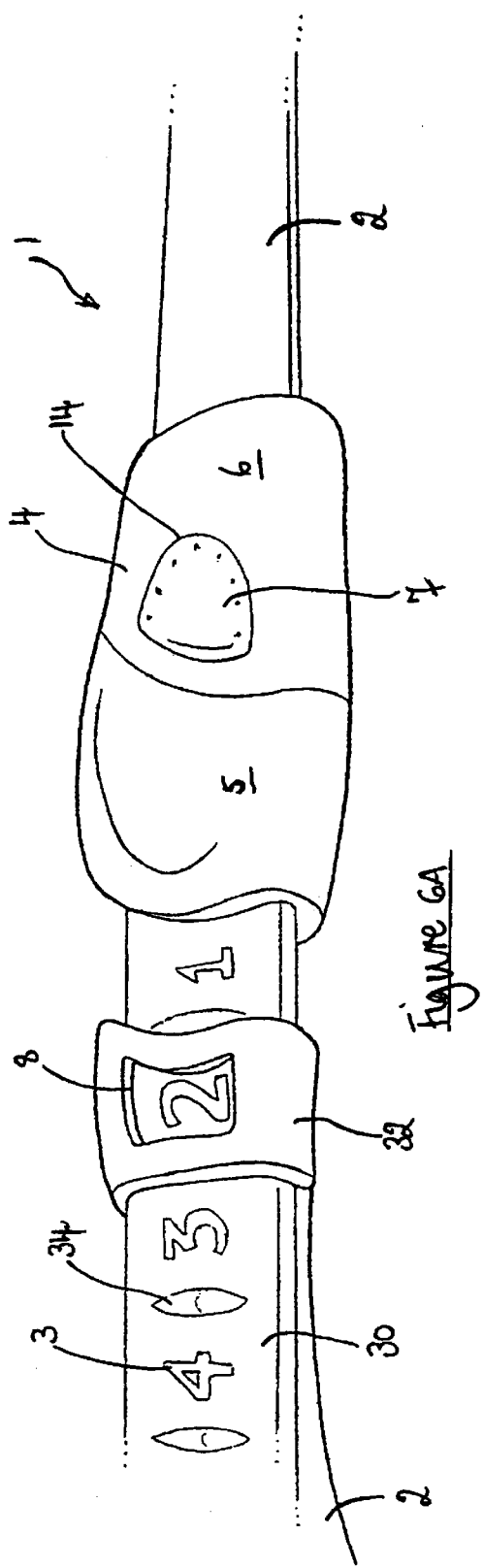
FIGS. 6A and 6B are perspective views of a fourth embodiment of the invention, showing the clasp portions connected (FIG. 6A) and disconnected (FIG. 6B)
Figure 6B:
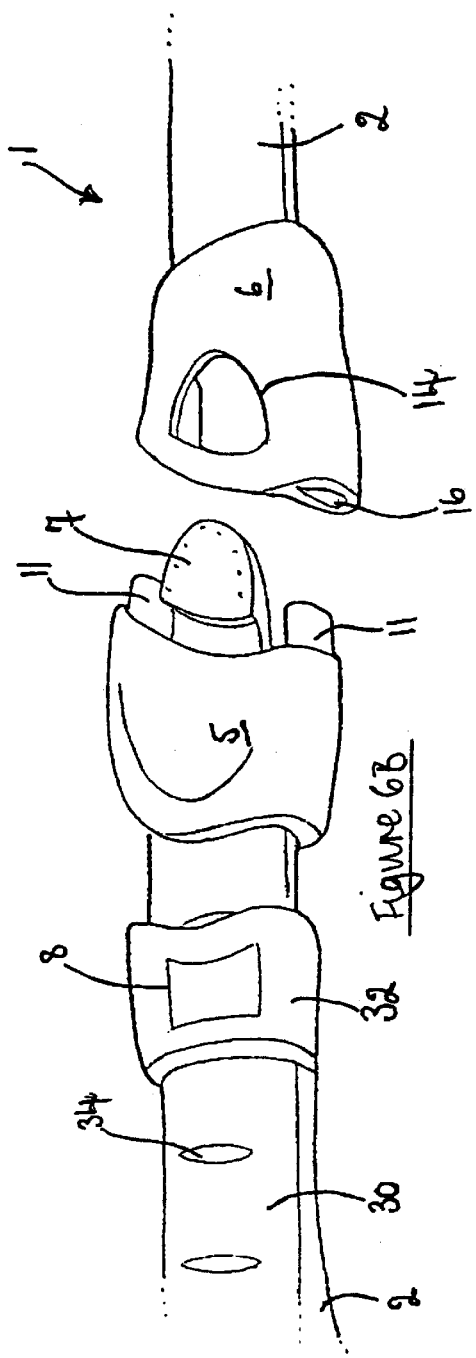

A fourth embodiment of the measuring device, as shown in FIGS. 6A and 6B, has a clasp 4 that works like the clasp 4 shown in FIG. 1, in that a tongue 7 and lugs 11 co-operate with a corresponding hole 14 and recesses 16 when the male and female portions 5, 6 are fastened together. However, a strip 30 is fixed inside the male portion 5 by fixing means (not shown) that can, for example, correspond to the fixing bar 17 shown in the female portion 6 in FIG. 2.

As with the measuring device 1 shown in FIGS. 4 and 5, indicia 3 borne by the strip 30 are read through a window 8 in a sleeve 32 within which the strip 30 can slide. However, the strip 30 and the sleeve 32 of FIGS. 6A and 6B include the further refinement of detent means that encourage indexible movement of the strip 30 in relation to the sleeve 32. Specifically, in the embodiment shown, the strip includes transverse notches 34 that temporarily and resiliently interlock with corresponding tooth formations (not shown) inside the sleeve 32. In this way, the strip 30 slides in a stepwise manner through the sleeve 32 so that the strip 30 rests at predetermined equi-spaced positions. This ensures that the indicia 3 of the strip 30 are displayed in their entirety, rather than partially, within the window 8 in the sleeve 32. So, for example, where the indicia 3 is a series of numerals, the measurement is always expressed within the window 8 as a whole numeral rather than as a portion of a numeral, which could be unreadable.

It will be appreciated by those skilled in the art that the notch and tooth arrangement may take many forms, such as a sprung arm or pawl mechanism.

Figure 7A:
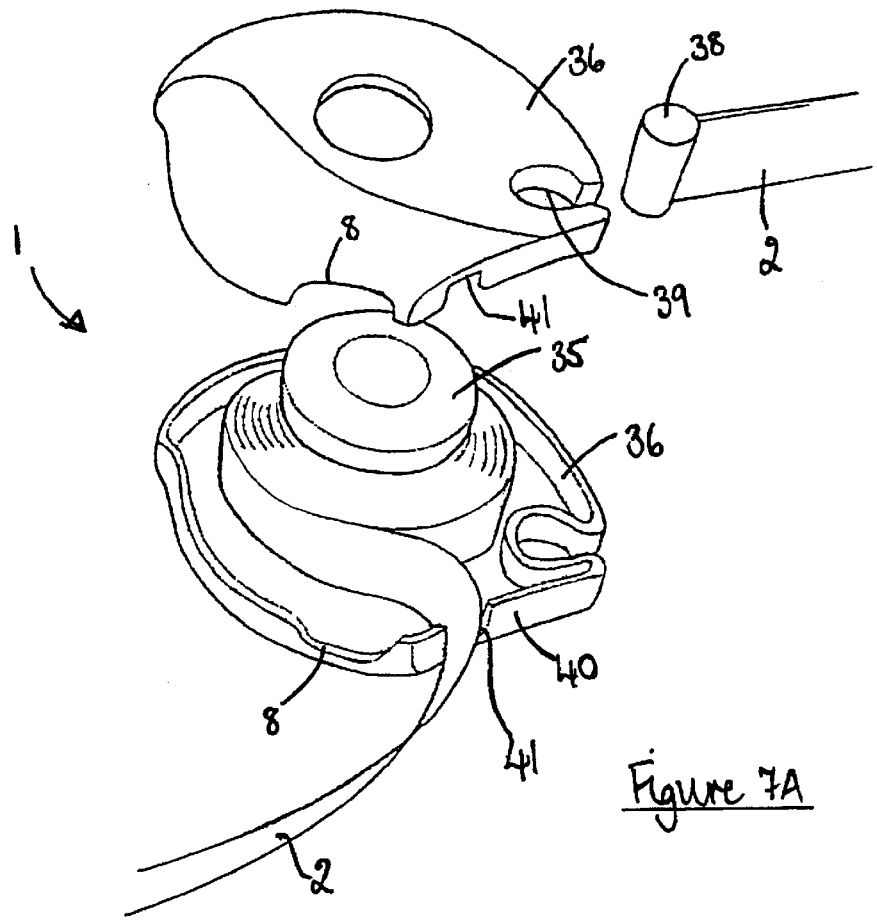
FIGS. 7A and 7B are perspective views of a fifth embodiment of the invention, being an exploded view (FIG. 7A) and an assembled view (FIG. 7B)
Figure 7B:
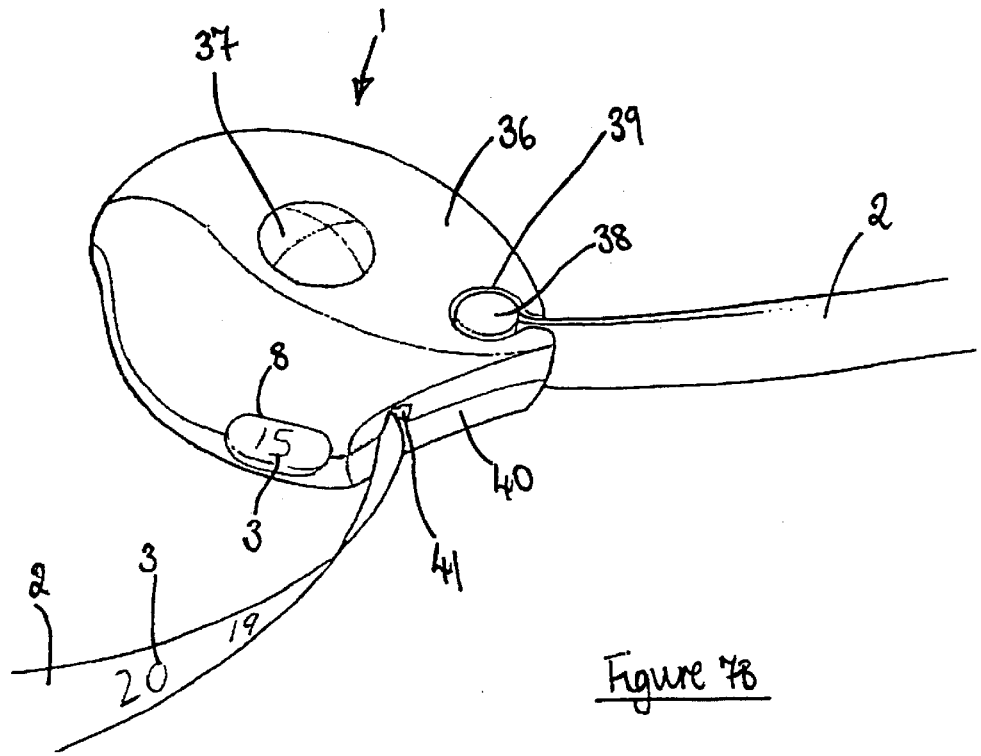
Figure 8A:
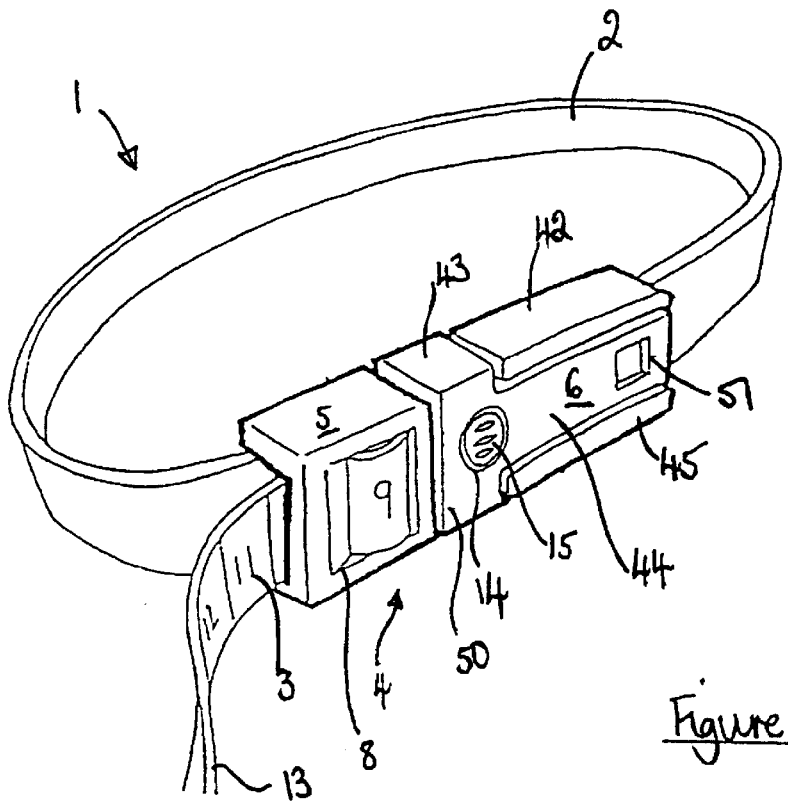
FIGS. 8A, 8B, 8C and 8D are perspective views of a sixth embodiment of the invention, FIG. 8A showing the strap fastened around a user's torso, FIG. 8B showing the strap being tensioned, FIG. 8C showing the tension increasing to a predetermined level and FIG. 8D showing the strap unfastened while displaying the measured torso girth.
Figure 8B:
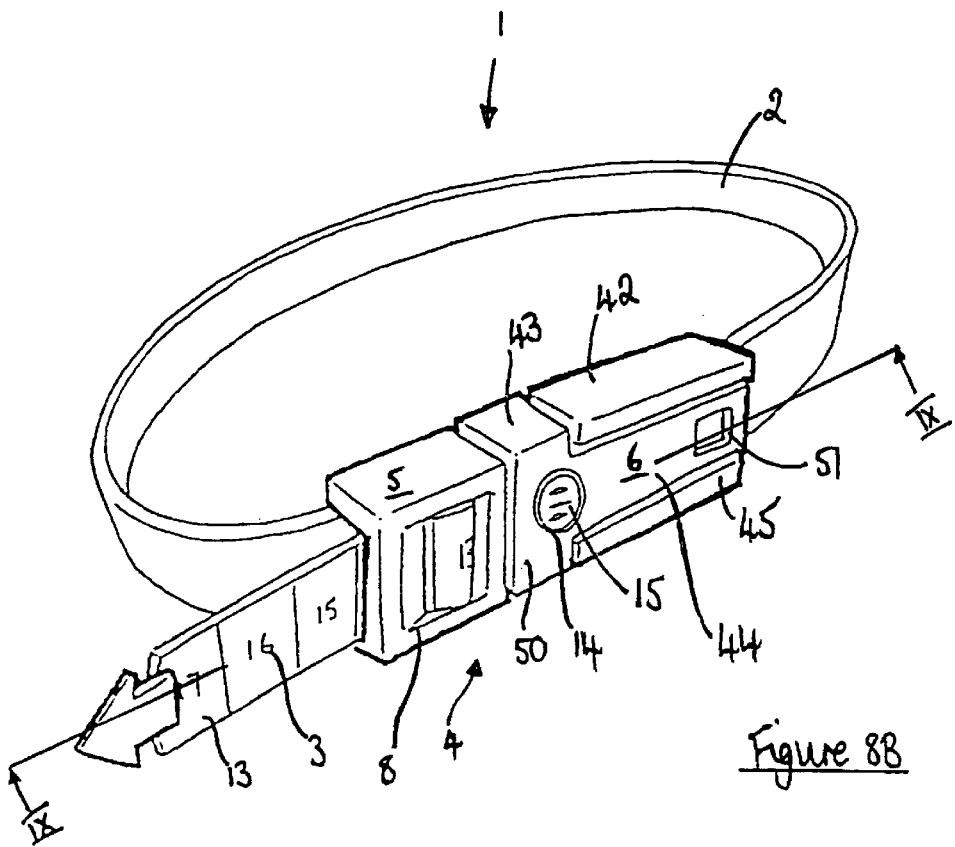
Figure 8C:
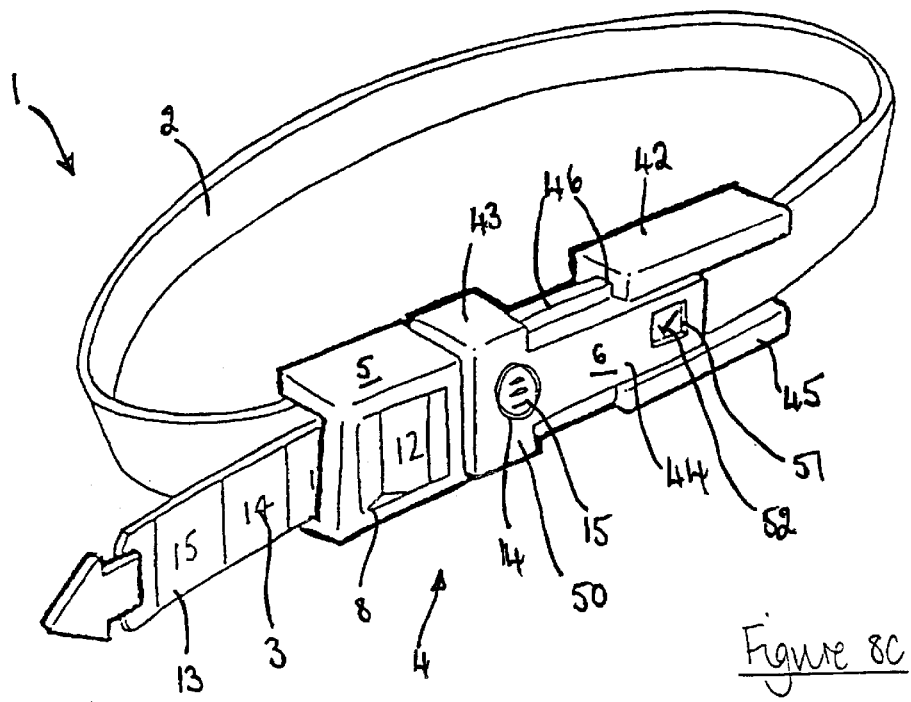
Figure 8D:
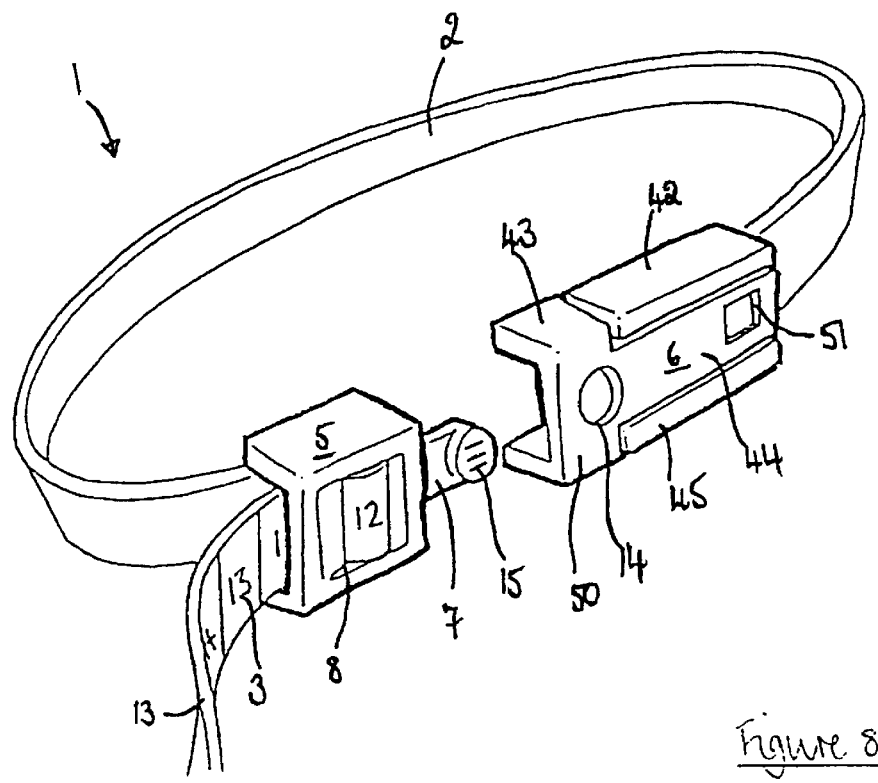

In a fifth embodiment shown in FIGS. 7A and B, the strap 2 is stored in a coil around a central spindle 35 within a housing 36 that emulates a retractable tape measure. Indeed, the spindle 35 includes spring means (not shown) for retracting a length of strap 2 deployed from the housing 36. The spindle 35 is capped by a button 37 which, when depressed, locks the strap 2 by engaging a ratchet mechanism (not shown) and prevents the strap 2 from being lengthened or retracted. The strap 2 is unlocked by tugging the free end of the strap 2 sharply away from the housing 36 to unlock the ratchet mechanism.

While one end of the strap 2 is fixed to the spindle 35, the other end of the strap 2 has a locating means in the form of a cylindrical peg 38. This peg 38 slots into a correspondingly-shaped groove 39 in the housing 36. The groove 39 is disposed at one end of a generally flat or shallowly concave surface 40 of the housing 36, the other end of which has an opening 41 communicating with the interior of the housing 36, through which the strap 2 passes on its way to and from the spindle 35. This surface 40 of the housing 36 lies against the user's torso in use of the measuring device 1.

To use the measuring device 1 of FIGS. 7A and B, the strap 2 is pulled out of the housing 36 through the opening 41 and passed around the torso and underneath the breasts. The peg 38 is slotted into the corresponding groove 39 against the retracting tension generated by the sprung spindle 35 and the strap 2 is further lengthened by the user expanding her rib cage. When the user's rib cage has been expanded to a suitable degree, the button 37 is depressed, locking the strap 2 at the length to which it has been extended. The peg 38 is removed from the groove 39 so that the measuring device 1 can be removed from the torso, and the appropriate indicia 3 borne by the strap 2 is read through a window 8 in the housing 36.

The measuring device 1 can easily be stored by pulling on the strap 2 to release the ratchet and thereby to allow the spring tension of the spindle 35 to retract the strap 2 into the housing 36. The peg 38 is larger than the opening 41 and so prevents the free end of the strap 2 from disappearing irretrievably into the housing 36.

The sixth embodiment of the invention, shown in FIGS. 8A, 8B, 8C, 8D, 9A and 9B includes an indicator that tells the user when the correct tension has been applied to the strap 2. As before, the measuring device 1 comprises a torso strap 2 with indicia 3 and a clasp 4 having a male portion 5 and a female portion 6. The male portion 5 has a resiliently flexible tongue 7 having a protruding button 15 that engages within a hole 14 in the female portion 6, and a window 8 through which girth indicia 3 on the strap 2 may be read. Also, as shown in the sectional views of FIGS. 9A and 9B, the strap 2 is looped around a holding bar 9 inside the male portion 6. The holding bar 9 lies behind the window 8 where it is hidden by the strap 2, and interacts with gripping formations 10 defined by the opposed sides of the window aperture 8. In this way tension is maintained in the strap 2 but the strap 2 can slide within and with respect to the male portion 5 under pressure of an expanding torso.

The female portion 6 is in two main parts, namely a body 42 and a carriage 43 that are movable longitudinally with respect to each other. The body 42 is fixed to an end of the strap 2 by the fixing pillar 28 shown in FIGS. 9A and 9B, which pillar 28 is situated some distance in from the end of the body 42, and the carriage 43 defines the hole 14 that, in use, receives the button 15 on the tongue 7 of the male portion 6. The body 42 is generally of U-section and the carriage 43 is generally of T-shape, and the parts are assembled such that the stem 44 of the T-shaped carriage 43 is embraced by the arms 45 of the U-section body 42. Sliding movement between the body 42 and the carriage 43 is possible along the longitudinal axis defined by the stem 44 of the T-shaped carriage 43 and is effected by means of co-operating interlocking slider formations 46 on the carriage 43 and in the body 42, the stem 44 of the carriage 43 sliding within the arms 45 of the body 42.

The longitudinal axis defined by the stem 44 of the carriage 43 is aligned with the strap 2. It will therefore be evident that when the strap 2 is under tension and the male and female portions 5, 6 are fastened together in use, the female portion 6 defined by the assembly of the body 42 and the carriage 43 tends to extend in length. This extension can be appreciated by comparing the clasp 4 in FIGS. 8B and 8C.

Figure 9A:
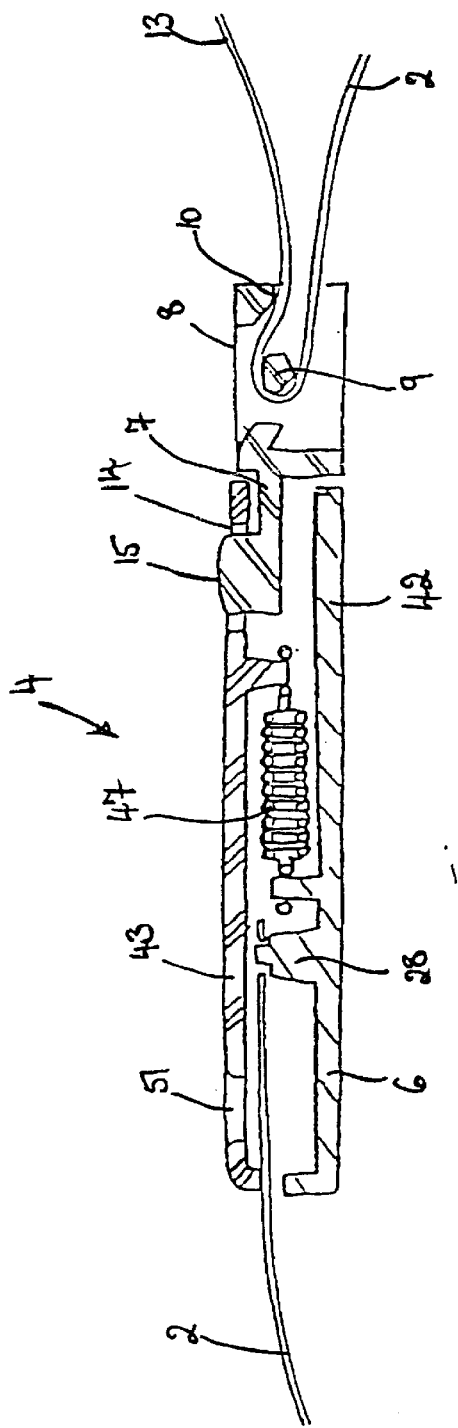
FIGS. 9A and 9B are longitudinal cross-section views along line IX—IX of FIGS. 8B and 8C showing how tension indicating means act during the increasing tension illustrated in FIGS. 8B and 8C.
Figure 9B:
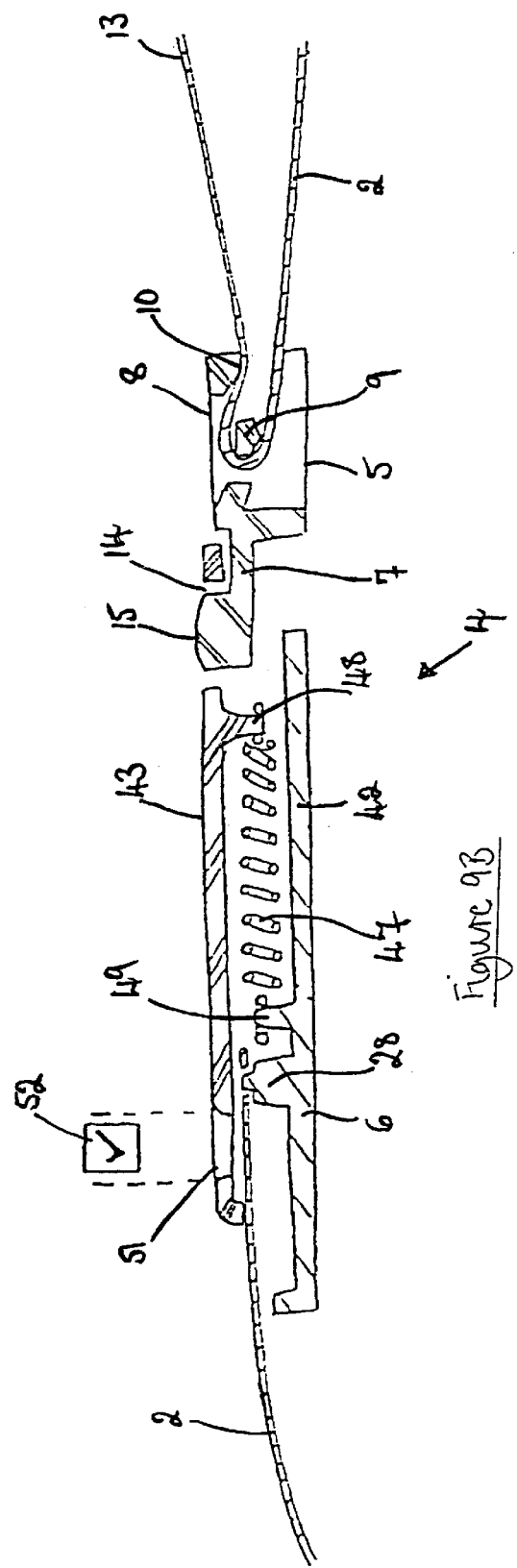

Referring now also to the sectional detail views of the female portion 6 in FIGS. 9A and 9B, the stem 44 of the carriage 43 overlies the central portion of the U-section body and conceals a tension spring 47 that is anchored at one end to a first pillar 48 moulded integrally with the carriage 43 and a second pillar 49 moulded integrally with the body 42. The tension spring 47 stretches as the female portion 6 extends under tension from the strap 2 as aforesaid, and biases the female portion 6 closed when strap tension is released.

As mentioned, the carriage 43 defines the hole 14 that, in use, receives the button 15 on the tongue 7 of the male portion 5 when the male and female portions 5, 6 of the clasp 4 are fastened together. This hole 14 is situated at the intersection between the stem 44 and cross-bar 50 of the T-shaped carriage 43. The carriage 43 also includes a window 51 through which tension indicia 52 on the strap 2 may be read, the tension indicia 52 extending from the end of the strap 2 that is fixed to the fixing pillar 49 in the body part 42 of the female portion 6, or being situated near the end of that strap 2. Thus, as the female portion 6 expands in use and hence the carriage 43 slides with respect to the body 42, the window 51 defined by the carriage 43 traverses the short portion of the strap 2 that is situated between the fixing pillar 49 and the end of the body 42, and either traverses an array of tension indicia 52 extending along that portion of the strap 2 or aligns with tension indicia 52 spaced from the end of the strap 2.

The elongation characteristic of the spring 47 is selected so that when the load reaches a predetermined level corresponding to a tension within the strap 2 that is deemed to be consistent with comfort, the window 51 is aligned with specific tension indicia 52 to indicate this comfort point to the user. Accordingly, when the strap 2 has been fastened around the user's torso and placed under appropriate tension, the indicia 52 confirms that there is comfortable tension in the device 1 as a whole.

The measuring device 1 of FIGS. 8A, 8B, 8C, 8D, 9A and 9B is used in much the same way as the measuring devices of the preceding Figures. The strap 2 is passed around the torso and underneath the breasts, the clasp 4 is fastened at the front of the user and the device 1 is loosely tensioned by pulling the free end 13 of the strap 2 away from the male portion 5 of the clasp 4. Once the device 1 is loosely tensioned, the user breathes normally while gently pulling on the free end 13 until the tension indicia 52 shown in window 51 indicates that the correct tension has been reached. Once this point is reached, the user stops tensioning the strap 2 (which is then held by friction by the holding bar 9 in the male portion 5 of the clasp 4), releases the clasp 4 and reads the indicia 3 indicated in window 8. In this way, the rib cage is not expanded to an arbitrary degree and the comfort of the torso strap 2 can be ascertained while the chest is in a normal state.

The tension indicia 52 may be in the form of confirmatory indicia, such as a tick (√) and/or green colour. If the strap 2 is tensioned too tightly, the indicia 52 may change from being confirmatory to inhibitory, for example by way of a cross (X) and/or red colour. Alternatively, the female portion 6 may include a stop (not shown) which prevents the strap 2 from being pulled any tighter.

In addition to ensuring comfort, the device illustrated in this embodiment very simply provides consistency of girth measurement that is difficult to achieve when encircling a compressible body such as a torso. As mentioned above, the problem is that pulling on a strap 2 to ensure that it is taut compresses the body encircled by the strap 2, and so the girth of the body will change as a result of the measurement process. This introduces self-defeating inaccuracy unless a consistent degree of compression is created and allowed for. The device also considers and takes into account the effect of bra elasticity, thereby ensuring the comfort and support required of a bra.

Figure 10:
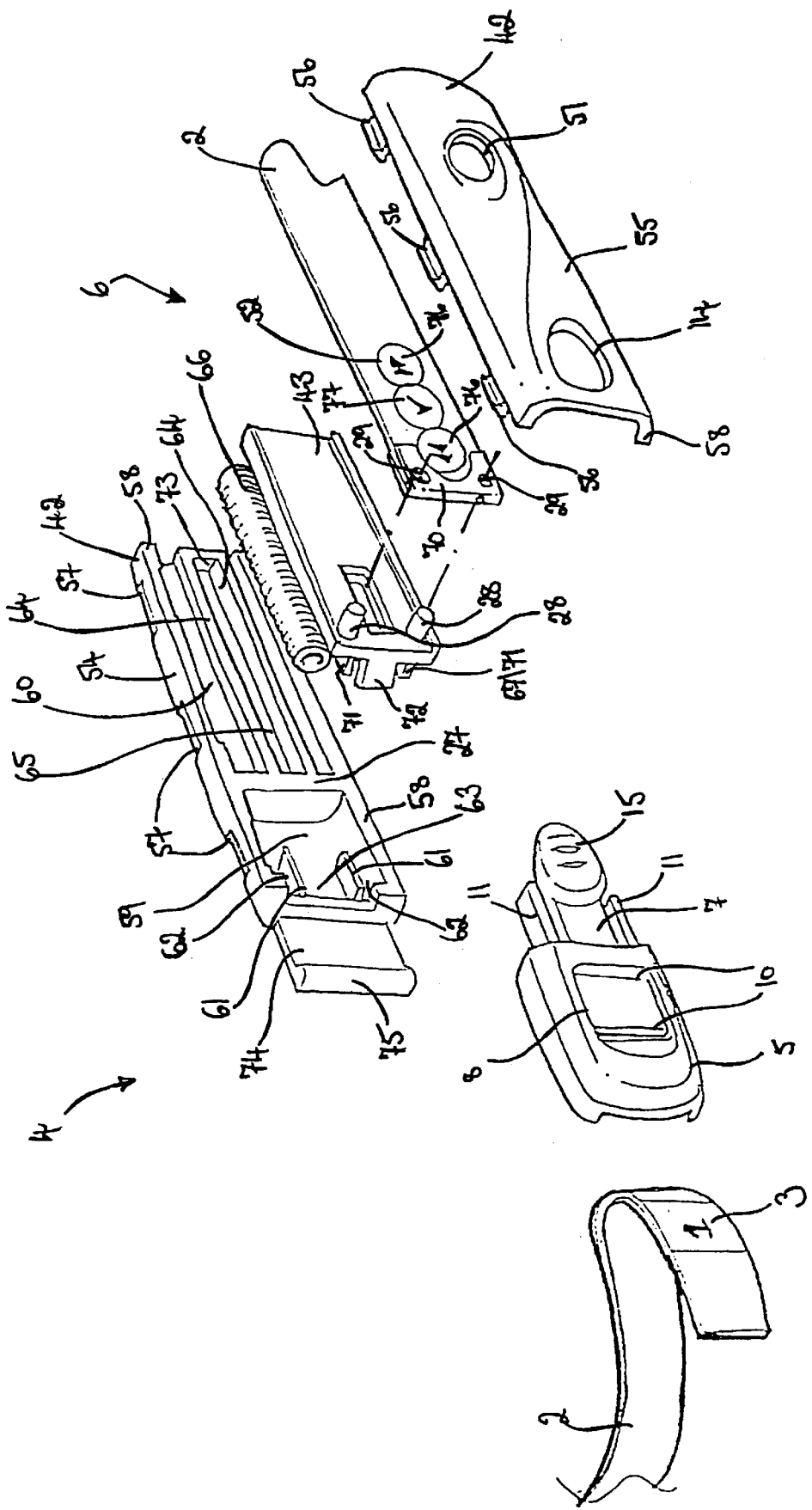
FIG. 10 is an exploded perspective view of a seventh embodiment of the invention.

However, it will be appreciated that the body 42 and carriage 43 may be embodied in different forms, for example as shown in FIG. 10. While the U- and T-shapes of the body 42 and carriage 43 in FIGS. 8A, 8B, 8C, 8D, 9A and 9B are simple to manufacture, assemble and use, there is a small risk that the user's flesh may become trapped between the moving parts, thus pinching the user in a potentially sensitive place. Therefore, the seventh embodiment, shown in FIG. 10, is designed to alleviate this problem.

FIG. 10 shows a measuring device 1 with a clasp 4 that is similar to the clasp shown in FIGS. 8A, 8B, 8C, 8D, 9A and 9B. As before, like numerals are used for like parts. It will be noted that the male portion 5 is akin to the male portion 5 of FIG. 8, having a resiliently flexible tongue 7 with a protruding button 15 that engages within a hole 14 in the female portion 6, two lugs 11 disposed one each side of the tongue 7 and a window 8 through which girth indicia 3 on the torso strap 2 may be read. As in the sixth embodiment, the strap 2 is fixed around a fixing bar (not shown) located behind the window 8 inside the male portion 5. Tension in the strap 2 is maintained by gripping formations 10 defined by opposite sides of the window aperture.

Like the sixth embodiment, the female portion 6 of the seventh embodiment has a body 42 and a carriage 43 that are movable longitudinally with respect to each other. However, in the seventh embodiment, the body 42 is in two parts having a base 54 and a lid 55 that, when assembled, surround the carriage 43, being held together by tabs 56 extending from the lid 55 that snap-fit into slots 57 in the base 54. The base 54 and the lid 55 comprise co-operating peripheral walls 58 defining respective hollow interiors divided by a transverse partition 27 upstanding from the base. Thus, when assembled by snap-fit as described, the base 54 and lid 55 define two cavities disposed end-to-end, divided by the partition. The first of these cavities 59 is adapted to receive the proximal end of the male portion S (i.e. the tongue 7 flanked by the two lugs 11), with an enlarged button 15 on the free end of the tongue 7 engaging within the hole 14. The second of these cavities 60 is adapted to receive, house and support the carriage 43 for reciprocal movement within that second cavity 60.

The first cavity 59 includes a pair of longitudinal partitions 61 also upstanding from the base 54 that, together with the opposed part of the peripheral wall 58, define respective channels 62 for receiving the respective lugs 11 on the male portion 5. The gap between the partitions defines an aperture 63 that receives the tongue 7 of the male portion 5.

The second cavity 60 also has a pair of longitudinal partitions 64 upstanding from the base 64, in this case defining a central longitudinal groove 65 extending along the length of the second cavity 60. The longitudinal groove 65 receives a compression spring 66 acting on the carriage 43 and the body 42 and, together with the partitions 64, co-operates with guide formations 67 on the carriage 43 so as to guide its reciprocal movement with respect to the body 42.

The carriage 43 is shaped to fit within the second cavity 60 and is generally flat and oblong, save for the aforementioned guide formations 67 on a first face of the carriage and a pair of fixing pillars 28 upstanding from each corner of the proximal end on a second opposed face 69 of the carriage, namely the face facing the lid 55 of the body 42. The fixing pillars 28 are received within corresponding holes 29 at the end of the strap 2 to be connected to the female portion 6: the end of the strap 2 is surrounded by a crimped metal reinforcement 70 to prevent the strap 2 tearing around the holes 29. When the strap 2 is secured to the fixing pillars 28 in this way, the strap 2 is secured within the body 42 when the lid 55 is snap-fitted closed onto the base 54.

The guide formations 67 on the first face of the carriage 43, the face that faces the base 54 of the body 42, comprise two longitudinal flanges 71 and a transverse projection 72. The longitudinal flanges 71 extend along the length of the carriage 43 and, on assembly, slidingly embrace the pair of longitudinal partitions 64 that define the central groove 65. The transverse projection 72 depends from the proximal end of the carriage 43 and is shaped to fit closely into the central groove 65. A compression spring 66 lying in the central groove 65 acts between the projection 72 and a closed distal end 73 of the groove 65. The closed end 73 of the groove 65 co-operates with the spring 66 to prevent the carriage 43 being pulled out of and disconnected from the body 42.

When the device 1 is fastened around the user's torso by inserting the male portion 5 into the female portion 6, it will be noted that a distal extension 74 of the female portion 6 extends behind the window part 8 of the male portion 5. As such, the distal extension 74 lies between the user's torso and the portion of the strap 2 that is threaded into the male portion 5. In this way, the distal extension 74 prevents that portion of the strap 2 pinching the user's flesh as the strap 2 moves with respect to the male portion 5. It will also be noted that the free end of the distal extension terminates in an enlarged lip 75. When the clasp 4 is fastened together, this lip 75 bears against the portion of the strap 2 threaded into the male portion 5 to resist slippage of the strap 2 with respect to the male portion 5.

In use, when the strap 2 is under tension, the strap 2 causes the carriage 43 to slide with respect to the body 42 against the bias of the compression spring 66 until indicia 52 on the end of the strap 2 aligns with a window 51 in the lid 55 of the body 42 to indicate the tension in the strap 2. As described for the tension spring 47 in the sixth embodiment, the compression characteristic of the compression spring 66 in the seventh embodiment is selected so that when the compression reaches a predetermined level corresponding to a tension within the strap 2 that is deemed to be consistent with comfort, the window 51 is aligned with specific tension indicia 52 to indicate this comfort point. As FIG. 10 shows, the indicia 52 can comprise inhibitory indicia 76, in this case in the form of arrows, on each side of confirmatory indicia 77, in this case in the form of a tick. The arrows 76 indicate the direction in which the strap 2 must move in order to display the tick 77, thereby to confirm that there is comfortable tension in the device as a whole.

As has been made clear, the measuring tape of the invention has wide application in that it can be used to measure the circumference of different parts of the body. This presents a challenge in variants of the invention that employ a tension indicator, because the tension deemed to be correct for measuring one part of the body might be different to that deemed to be correct for measuring another part of the body. Accordingly, the tension indicators may be adapted to indicate different levels of tension as being correct. There are two principal ways of doing so.

One way of adapting a tension indicator to indicate different levels of tension is to have a series of indicia corresponding to successively increasing or decreasing tensions (for example, different lengths of the spring), each of the indicia being marked as appropriate. Preferably, the indicia represent the part of the body for which the corresponding tensions are appropriate, such as the words 'chest', 'neck', 'arm' or 'leg', or associated pictograms.

Another way of adapting a tension indicator to indicate different levels of tension is to change the characteristics of the spring so that different tensions display the same indicia. For example, the effective length of the spring can be varied so that different tensions result in the same extension. This can be achieved by providing one or more pawls that selectably engage the spring, the or each pawl being movable inwardly from beside the spring to lie between successive coils of the spring when selected. The or each pawl can be moved inwardly into engagement with the spring by one or more user-operable push-buttons on the housing that surrounds the spring. In this way, when selected by pressing a corresponding button, a pawl prevents extension of the part of the spring blocked by the pawl, while allowing the remainder of the spring to extend, thus shortening the effective length of the spring.

Where a plurality of pawls are provided, these may be spaced along the length of the spring so that each represents a different effective spring length, each being selectable by pressing a respective button. Again, preferably, the buttons have associated indicia representing the part of the body for which the corresponding tensions are appropriate, such as the words 'chest', 'neck', 'arm' or 'leg', or associated pictograms. When it is desired to change the effective spring length, a button can be pulled out to disengage its pawl from the spring and another button pushed in, or the spring can be left with its full effective length by leaving all pawls disengaged.

In general, those skilled in the art will appreciate that the present invention may be embodied in other specific forms without departing from its spirit or essential attributes. For example, while it is preferred that the strap 2 is made from extruded plastics, it may be manufactured from other suitable materials including fabric. Such plastics or fabrics may be elastic and/or of non-slip characteristics.

It will be appreciated that the attachment of the strap 2 to the male and female portions 5, 6 of the clasp 4 need not necessarily be in the order described. Also, although not ideal, the clasp 4 may be done up behind the user's back.

It will also be clear to those skilled in the art that an elastic band or other resilient bias means could be used in place of a spring.

Also, the indicia 3 are generally shown as being numeric in the preceding Figures. However, the numerals need not correspond to any specific units, such as inches or centimetres. Furthermore, colours, characters or icons could be used in place of numerals. For example, the indicia could be a series of coloured regions, each colour corresponding to a particular torso size. Intermediate regions of the sequence may be a combination of colours in the neighbouring blocks, e.g. red, red/blue stripes, blue.

It is notable in this respect that colour-based indicia will work well whether viewed over one's shoulder with one or two mirrors or from above. Conversely, numerals or other characters would only work properly when viewed with two mirrors or with a device that is fastened at the front of the user, because unless themselves expressed in mirror writing, numerals depend upon the mirror-image reversal of one mirror to be corrected by the other mirror.

Figure 11:
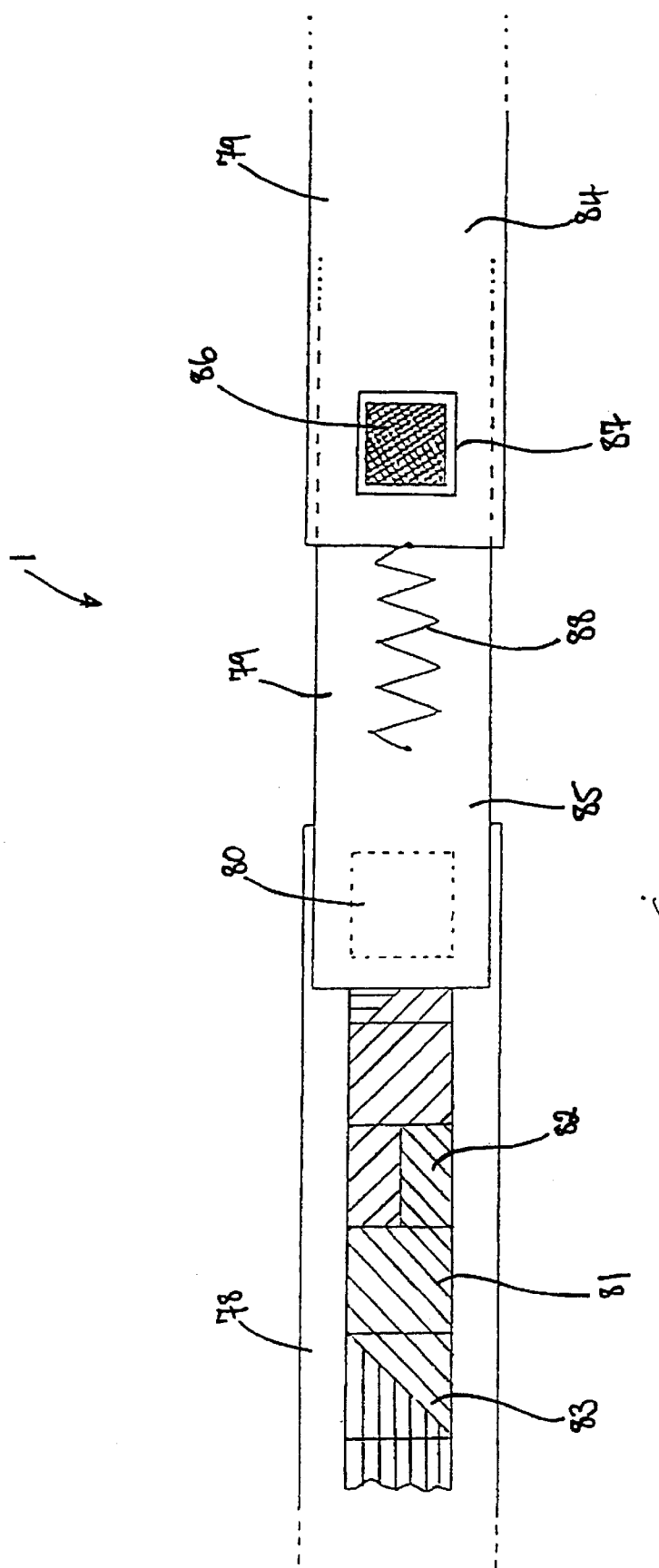
FIG. 11 is a detail plan view of an eighth embodiment of the invention.

An example of a torso strap suitable for rear fastening and having a colour scale is illustrated in the eighth embodiment of the invention shown in FIG. 11. The device 1 comprises opposed first and second strap portions 78, 79 whose ends can be fastened together by hook-and-eye pads such as Velcro® 80 when the ends are in overlapping relation as shown. The strap portions 78, 79 have indicia 81, in this case a series of coloured rectangles disposed along the first strap portion 78, that can be read by a user to indicate the length of the fastened strap 2 when a rectangle 81 is aligned with the free end of the second strap portion 79.

FIG. 11 shows a technique for colouring an intermediate block among the indicia 81. This is to divide such a block into two regions, the colour of each region corresponding to the colour of each respective neighbouring block. This can be achieved in different ways, one way (shown by block 82 in FIG. 11) being to divide the block into oblong halves divided by a longitudinal border and another way (shown by block 83 in FIG. 11) being to divide the block into triangular halves divided by a diagonal border. An advantage of the latter arrangement is that the proportion of one colour to another exposed in use varies in accordance with the longitudinal relative positions of the strap portions 78, 79.

One of the strap portions 79 is itself divided into portions. These latter portions will be described as upper and lower portions 84, 85 in this instance because these portions, too, overlap, albeit in a manner that permits the upper portion 84 to slide over the lower portion 85. The lower portion 84 is marked with a rectangular indicator 86 and the upper portion 84 is penetrated by a rectangular window 87 of similar size through which the whole of the indicator 86 can be viewed when the window 87 and the indicator 86 are aligned with each other. When the window 87 and the indicator 86 are slightly misaligned, only part of the indicator 86 is visible in the window 87 together with some neighbouring background of the lower portion 85. This indicates the direction of relative movement necessary to achieve proper alignment.

The free end of the upper portion 84 is linked to an intermediate part of the lower portion 85 by a spring 88 that transmits a tensile load from the upper portion 84 to the lower portion 85 when the second strap portion 79 is pulled taut. The spring 88 acts in the same way as described for the sixth embodiment of the invention, namely that when the load reaches a predetermined level corresponding to a tension within the second strap portion 79 that is deemed to be consistent with comfort, the indicator 86 is aligned with the window 87 to indicate this comfort point to the user.

Although shown in FIG. 11 with the free ends of the straps 78, 79 fixed to one another by hook-and-eye pads such as Velcro® 80, those skilled in the art will see how a slipping link or fastening of the type described in any of the preceding Figures can be applied to the strap of FIG. 11.

In view of these and other variants, reference should be made to the appended claims and other general or conceptual statements herein rather than to the foregoing specific description as indicating the scope of the invention.

What is claimed is:

1. A measuring tape for measuring the girth of any part of a user's body, the tape comprising a separable fastening that, when fastened, creates a loop of tape that extends in use around the user's body part without support from the user's hands, a link co-operable with the tape allowing the circumference of the loop to be adjusted or varied when around the user's body part, and girth indicia co-operable with the link to indicate the circumference of the loop, wherein the link maintains a securing tension on the loop to secure the loop around the body part but allows expansion of the loop when the user expands his or her body part during said measurement, and resists variation of the loop circumference when the fastening is unfastened after use so that the circumference of the loop can be read by the user after use with reference to the girth indicia.

2. A measuring tape as claimed in claim 1, wherein the link is integral with the fastening.

3. A measuring tape as claimed in claim 1, wherein the girth indicia are situated on the tape.

4. A measuring tape as claimed in claim 1, wherein the link is separate from the fastening and is connected to the fastening by a strip movable with respect to the link, the girth indicia being situated on the strip.

5. A measuring tape as claimed in claim 1, wherein the link includes a display area with which indicia can align to be displayed.

6. A measuring tape as claimed in claim 5, wherein the display area is a window or cut-out.

7. A measuring tape as claimed in claim 1, wherein the link is a slipping link that allows slippage of the tape to allow expansion of the loop while maintaining the securing tension, but grips the tape to an extent necessary to prevent slippage of the tape when the fastening is unfastened after use.

8. A measuring tape as claimed in claim 7, wherein the slipping link includes a holding bar around which the tape is looped and one or more gripping formations bearing upon the tape looped around the bar.

9. A measuring tape as claimed in claim 1, wherein the link is a store of tape that retracts tape on contraction of the loop and pays out tape on expansion of the loop.

10. A measuring tape as claimed in claim 9, wherein the store of tape is a reel biased to retract the tape.

11. A measuring tape as claimed in claim 1, wherein the link is adapted for indexible movement of the tape between discrete detent positions.

12. A measuring tape as claimed in claim 11, wherein the detent positions correspond to the spacing between successive indicia.

13. A measuring tape as claimed in claim 1, further including a tension indicator for indicating tension in the loop.

14. A measuring tape as claimed in claim 13, wherein the tension indicator comprises first and second parts linked by resilient bias means for relative movement against bias when the loop is under circumferential or longitudinal tension, and a visual indicator responsive to the extent of said relative movement.

15. A measuring tape as claimed in claim 14, wherein the visual indicator comprises co-operable tension indicia that are brought into mutual alignment by said relative movement when the tape is at a predetermined, tension.

16. A measuring tape as claimed in claim 15, wherein tension indicia associated with one of said parts of the tension indicator are relatively movable into alignment with a window, cut-out or indicating indicia on the other of said parts of the tension indicator.

17. A measuring tape as claimed in claim 16, wherein the first part includes a window or cut-out and the second portion includes an indicator aligned with and visible through that window or cut-out when the tape is at the predetermined tension.

18. A measuring tape as claimed in claim 17, wherein the indicator is at least partially hidden by the first portion when the tape is not at the predetermined tension.

19. A measuring tape as claimed in claim 16, wherein the tension indicia is situated on a portion of tape attached to one of said parts of the tension indicator.

20. A measuring tape as claimed in claim 14, wherein the first and second parts overlap.

21. A measuring tape as claimed in claim 13, wherein the tension indicator is integral with the fastening.

22. A method for measuring the girth of any part of a user's body, comprising fastening a loop of tape around the user's body part without support from the user's hands, creating and maintaining a securing tension on the loop to secure the loop around the body part, permitting expansion of the loop when the user expands his or her body part during said measurement, unfastening the loop while maintaining the loop circumference, and reading the circumference of the loop after use.

23. A method as claimed in claim 22, further comprising viewing a visual indication of the circumferential or longitudinal tension in the loop.

24. A method as claimed in claim 23, further comprising responding to the visual indication by adjusting the tension in the loop to achieve an indicated predetermined tension.

* * * * *

UNITED STATES PATENT AND TRADEMARK OFFICE
CERTIFICATE OF CORRECTION

PATENT NO. : 6,640,460 B1
DATED : November 4, 2003
INVENTOR(S) : Nabarro et al.

It is certified that error appears in the above-identified patent and that said Letters Patent is hereby corrected as shown below:

Title page,
Item [57], ABSTRACT,
Line 15, "indicia A method" should read -- indicia. A method --;

Column 1,
Line 30, "is required This" should read -- is required. This --;

Column 2,
Line 58, "imputed from t he" should read -- imputed from the --;

Column 4,
Line 61, "indicia Indexing movement" should read -- indicia. Indexing movement --;

Column 11,
Line 54, "the male portion S" should read -- the male portion 5 --;

Column 16,
Line 13, "at a predetermined, tension" should read -- at a predetermined tension --.

Signed and Sealed this

Sixteenth Day of March, 2004

JON W. DUDAS
*Acting Director of the United States Patent and Trademark Office*